(12) United States Patent
Jessop

(10) Patent No.: US 7,214,539 B2
(45) Date of Patent: May 8, 2007

(54) SCINTILLATION PROXIMITY TEST

(75) Inventor: Robert A. Jessop, Thornhill (GB)

(73) Assignee: GE Healthcare Limited, Amersham (GB)

( * ) Notice: Subject to any disclaimer, the term of this patent is extended or adjusted under 35 U.S.C. 154(b) by 0 days.

(21) Appl. No.: 11/356,688

(22) Filed: Feb. 17, 2006

(65) Prior Publication Data

US 2006/0141536 A1    Jun. 29, 2006

Related U.S. Application Data

(60) Continuation of application No. 10/319,305, filed on Dec. 13, 2002, now Pat. No. 7,081,365, which is a division of application No. 09/485,954, filed as application No. PCT/GB98/02459 on Aug. 17, 1998, now Pat. No. 6,524,786.

(30) Foreign Application Priority Data

Aug. 18, 1997 (GB) ............................... 97306264.9

(51) Int. Cl.
  G01N 33/24   (2006.01)
  C12Q 1/00    (2006.01)
  H05B 33/00   (2006.01)
  A61B 6/00    (2006.01)

(52) U.S. Cl. .................... 436/82; 436/81; 435/4; 250/484.2; 250/582

(58) Field of Classification Search ............ 435/4; 250/485.1, 486.1, 487.1, 484.2, 582; 422/68.1; 436/82, 81
See application file for complete search history.

(56) References Cited

U.S. PATENT DOCUMENTS

| | | | |
|---|---|---|---|
| 4,415,808 A | 11/1983 | Cusano et al. | |
| 4,922,092 A * | 5/1990 | Rushbrooke et al. | 250/214 VT |
| 5,435,937 A | 7/1995 | Bell et al. | |
| 5,698,397 A | 12/1997 | Zarling et al. | |
| 5,961,923 A | 10/1999 | Nova et al. | |
| 6,120,902 A | 9/2000 | Van Havenbergh et al. | |
| 6,198,577 B1 | 3/2001 | Kedar et al. | |
| 6,524,786 B1 * | 2/2003 | Jessop | 435/4 |

FOREIGN PATENT DOCUMENTS

| | | |
|---|---|---|
| EP | 0 214 713 | 3/1987 |
| EP | 0 556 005 | 8/1993 |
| EP | 0 744 451 | 7/1999 |
| WO | WO 91/08489 | 6/1991 |
| WO | WO 94/26413 | 11/1994 |

OTHER PUBLICATIONS

Beverloo, H., et al., "Preparation and Microscopic Visualization of Multicolor Luminescent Immunophosphors", *Cytometry*, vol. 13, 1992, p. 561-570.

Blasse, G., et al., *Luminescent Materials*, Springer-Verlag, Berlin, 1994.

Englert, D., "Optical Detection Technology for Radioisotope and Non-Radioisotopic Assays", *The Society for Biomolecular Screening*, 1996, p. 209-221.

Hooper, C., et al., "Low-Light Imaging Technology in the Life Sciences", *J. Biolumin Chemilumin*, vol. 9, 1994, p. 113-122.

Patterson, S., et al., "Evaluation of Storage Phosphor Imaging for Quantitative Analysis of 2-D Gels Using the Quest II System", *BioTechniques*, vol. 15, No. 6, 1993, p. 1076-1083.

Tang, C., et al., "Localization and Quantification of Cholecystokinin Receptors in Rat Brain with Storage Phosphor Autoradiography", *BioTechniques*, vol. 18, No. 5, 1995, p. 886-889.

* cited by examiner

*Primary Examiner*—Long V. Le
*Assistant Examiner*—Shafiqul Haq
(74) *Attorney, Agent, or Firm*—Yonggang Ji

(57) ABSTRACT

The invention concerns scintillation proximity assays performed in multiwell plates where a charge coupled device is used to image the wells. Conventional phosphors emit blue light (350–450 nm) which is absorbed by yellow or brown assay components. This problem is addressed by the use of phosphors that emit radiation of longer wavelength (480–900 nm).

10 Claims, 6 Drawing Sheets

SCINTILLATION PROXIMITY TEST

CROSS REFERENCE TO RELATED APPLICATIONS

This application is a continuation of U.S. patent application Ser. No. 10/319,305 filed Dec. 13, 2002, which is a divisional application of U.S. patent application Ser. No. 09/485,954 filed May 16, 2000, now U.S. Pat. No. 6,524,786, which is a filing under 35 U.S.C. §371 and claims priority to international patent application number PCT/GB98/02459 filed Aug. 17, 1998, which claims priority to patent application number 97306264.9 filed in Great Britain on Aug. 18, 1997; the disclosures of which are hereby incorporated by reference in their entireties.

BACKGROUND OF THE INVENTION

This invention concerns scintillation proximity tests, that is to say assays or other experiments involving the scintillation proximity principle.

Current scintillation proximity assay (SPA) technology involves the use of scintillant beads made from either cerium-doped yttrium silicate ($Y_2SiO_5$:Ce) (hereafter referred to simply as yttrium silicate or YSi) or polyvinyltoluene (PVT) containing an organic scintillant such as PPO. Assays are carried out in aqueous buffers using radioisotopes such as $^3H$, $^{125}I$, $^{14}C$, $^{35}S$ or $^{33}P$, that emit low-energy radiation, the energy of which is easily dissipated in an aqueous environment. For example, the electrons emitted by $^3H$ have an average energy of only 6 keV and have a very short path length (~1 μm) in water. If a molecule labelled with one of these isotopes is bound to the bead surface, either directly or via interaction with another molecule previously coupled to the bead, the emitted radiation will activate the scintillant and produce light. The amount of light produced, which is proportional to the amount of labelled molecules bound to the beads, can be measured conveniently with a liquid scintillation (LS) counter. If the labelled molecule is not attached to the bead surface, its radiation energy is absorbed by the surrounding aqueous solvent before it reaches the bead, and no light is produced. Thus, bound ligands give a scintillation signal, but free ligands do not, and the need for a time-consuming separation step, characteristic of conventional radioligand binding assays, is eliminated. The manipulations required in the assays are reduced to a few simple pipetting steps leading to better precision and reproducibility.

PCT WO 91/08489 (Packard Instrument Company Inc.) describes a support body for use in scintillation proximity radioimmunoassay, the support body being constructed of a scintillating material, having coupled to its surface a multiplicity of ligands such a antigens, antibodies, etc. capable of selectively binding a reactant of interest. Preferably the support bodies consist of yttrium silicate activated with an inorganic cerium salt such as the oxide, carbonate, or chloride.

WO 94/26413 concerns the study of cellular and biochemical processes in living cells or in components of cells. Specifically described are devices and methods for the study of cellular and biochemical processes, using the scintillation proximity principle.

The simplicity of the scintillation proximity format allows almost complete automation of assays using robotic sample processors and microtitre plate scintillation counters. Consequently, SPA technology is capable of high throughput, which is particularly valuable in the case of drug- or sample-screening assays. SP assays have been carried out routinely in 96-well microtitre plates which are counted 6 wells at a time in specially designed microtitre plate scintillation counters. The search for increasingly higher throughput has led the manufacturers of these counters to produce instruments capable of counting 12 wells at a time, thus doubling throughput. It has also seen the advent of 384-well plates, although at present these can still only be counted 12-wells at a time.

A problem associated with SPA is that of colour quenching, caused by the presence in the assay medium of coloured compounds that absorb the light emitted by the current SPA bead types. Colour quenching attenuates the signal, thereby decreasing signal to noise and hence the sensitivity. Many of the samples being screened by SPA assays are coloured and the majority of these are yellow or brown in colour and absorb light in the blue region of the visible spectrum. Both PVT- and $Y_2SiO_5$:Ce-based SPA beads emit light in the blue region (maximal emission normally in the range 350 nm–450 nm) and so are susceptible to this effect.

An alternative detection system suitable for use in low to ultra-low light level imaging applications in the biological and biomedical sciences is CCD (Charge Coupled Device) Detection which has been used, for example, in assays which involve chemiluminescent, bioluminescent and fluorescence detection. Applications include immunoassays (Hooper et al, J. Biolum. Chemilum., 9,113–122, (1994)), and the analysis of specific fluorescent dye-labelled nucleic acids by hybridisation following electrophoretic separation of nucleic acid samples (EP 214713 to Astromed Ltd.). Ultra low-light imaging using CCD technology is quantitative and fast and the new generation of imaging instruments which use CCD cameras for detectors can image the whole of a plate at once and so have great potential for increasing sample throughput compared with microtitre well plate scintillation counters. Area imaging, i.e. the simultaneous imaging by CCD of all wells in a microtitre well plate is considered to be particularly advantageous when used in conjunction with high well-density plates containing 96, 384, 864, or more wells, since the time required to make measurements is significantly reduced compared with conventional scintillation counting techniques.

Imaging technology, in particular area imaging, has also been applied to isotopically labelled materials as an alternative to autoradiography. This approach has been most widely used in applications such as the quantitative analysis of proteins by 2-D gel electrophoresis (Patterson, et al, Biotechniques, 15(6), 1076, (1993)) and receptor localisation (Tang, et al, Biotechniques, 18(5), 886, (1995)). An imaging plate, coated with a radiation sensitive agent (e.g. strontium sulphide/samarium/cerium or barium fluorobromide/europium) is exposed to a radiolabelled sample and an image is formed due to radiation incident on the lanthanide metal coating of the plate. Following exposure, the image is read by means of an imaging plate reader.

CCD detection of SPA counts has also been reported (Englert, D., Society for Biomolecular Screening, Second Annual Conference Oct. 14–17, (1996), pp 209–221) using PVT-based microspheres. However, the photon count from the SPA wells was not sensitive enough to enable usable results to be obtained, due to low light output of the beads, sub-optimal signal detection capability of the system, as well as quenching by coloured samples. For conventional scintillation counting, instruments can be calibrated to take into account colour quenching. However, in the case of CCD detection using conventional SPA beads and under normal assay conditions, the number of photons detected per disintegration was insufficient to enable determination of quenching levels and quench correction was not possible. To date there appear to be no reports of working assays in which sample detection and measurement was obtained using this technique.

SUMMARY OF THE INVENTION

The present invention seeks to overcome the dual problems of low sensitivity of current CCD-based detection as well as colour quench in conventional SPA bead technology. The invention provides use in a scintillation proximity test of a phosphor that has an emission maximum of 480 nm–900 nm, and of a charge coupled device for detecting radiation emitted by the phosphor.

A scintillation proximity test is a test in which a surface carrying a phosphor is contacted with a body of fluid containing a radioisotope. Part of the radioisotope becomes immobilised adjacent the surface; the remainder of the radioisotope remains dispersed or dissolved in the fluid. The mean free path of electrons or other particles or radiation resulting from radioactive disintegrations of the radioisotope are small relative to the dimensions of the body of fluid, whereby that part of the radioisotope immobilised adjacent the surface is capable of exciting phosphor carried by the surface, but that part of the radioisotope dispersed or dissolved in the fluid is generally too far from the surface to be capable of exciting phosphor carried by the surface.

The surface may be massive, as for example a wall of a vessel or wells of a multiwell or microtitre plate; or particulate, as for example threads or beads. The phosphor may be present as a coating applied on a pre-formed surface; or may be dispersed in or constitute or form part of the surface.

The test may be a chemical or biochemical assay, for example a competition assay such as an immunoassay or immunometric assay. Or the test may involve a study of living cells which are, or which become, attached to the surface carrying the phosphor. Any test system in which a radioisotope becomes partitioned between a solid phase and a liquid phase is in principle suitable for the method of the invention.

A radioisotope may be present in free form or combined form, e.g. as an atom or ion; this may be useful for example when it is desired to monitor the take up of the radioisotope by cells adhering to the surface carrying the phosphor. Or the radioisotope may be used to label an assay reagent; this may be useful for example when a labelled reagent is caused to compete with an unlabelled reagent for binding to another reagent immobilised on the surface carrying the phosphor.

A scintillation proximity test may be performed in a qualitative or more usually in a quantitative manner. For example, measurements may be performed in a static mode, as when the result of a competition assay is determined after a fixed time or at equilibrium. Alternatively a scintillation proximity assay may be performed in a dynamic mode, as when radiolabel uptake by cells is monitored in real time. WO 94/26413 describes a scintillating microtitre plate and methods for studying cellular processes in real time. The scintillating microtitre plate is marketed by Amersham Lifescience under the name Cytostar-T™.

The fluid is generally an aqueous or other liquid. The radioisotope is preferably one which emits electrons having a mean free path up to 2000 μm in aqueous media. These include isotopes commonly used in biochemistry such as $^3$H, $^{125}$I, $^{14}$C, $^{35}$S, $^{45}$Ca, $^{33}$P and $^{32}$P, but does not preclude the use of other radioisotopes such as $^{55}$Fe, $^{86}$Rb, $^{109}$Cd and $^{51}$Cr which also emit electrons within this range.

The scintillation proximity test is preferably performed in the wells of a multiwell plate e.g. a microtitre plate. The phosphor may be provided as beads dispensed into the wells of such a plate. Or the phosphor may be incorporated into the plate itself, either by direct incorporation into the plastic of the plate, or by coating, together with a binding agent. Examples of possible binding agents are calcium sulphate, as used in the manufacture of tlc plates, and low-melting plastics such as polystyrene or copolymers of α-methylstyrene and vinyltoluene. These devices may have 24, 96 or 384 wells as in existing plates or may have higher densities of wells such as 864, 1536, 2400 3456 or indeed any desired number. They can be used to perform cell-based or ligand binding assays in conjunction with CCD camera based imagers. The phosphor preferably has an emission maximum of 500 nm–700 nm, that is to say in the green or yellow or red region of the spectrum. The phosphors are stimulated by low energy electrons or other particles or radiation resulting from radioactive disintegrations of the radioisotope. These phosphors generally have a higher light output than PVT based SPA beads or $Y_2SiO_5$:Ce beads and enable SPA assays to be imaged successfully. Moreover, all sample wells of a microtitre well plate can be imaged simultaneously by means of CCD detection. The longer wavelength green or red emissions alleviate the colour quenching problem which is at its greatest in the blue region of the spectrum.

Some phosphors are commercially available for industrial applications, for example in cathode ray tube technology, lamp phosphors and X-ray phosphors. See for example Blasse and Grabmaier, Luminescent Materials, Springer-Verlag, Berlin, (1994) and U.S. Pat. No. 5,435,937. The preparation of charge-stabilised suspensions of small phosphor particles (e.g. yttrium oxysulphide-$Eu^{3+}$, yttrium oxysulphide-$Tb^{3+}$) and their coupling to antibodies to give immunoreactive conjugates has been described (Beverloo, et al, Cytometry, 13, 561–570 (1992)). The phosphor conjugates were used in immunocytochemical applications by binding to cells, followed by visualisation using a fluorescence microscope under UV light excitation. To date however, such phosphors have not been described for use in counting applications involving radioactive tracers, particularly SPA There are many suitable phosphors that may be used. Some consist of an inorganic host material doped with an activator. Examples of such host materials are yttrium silicate, yttrium oxide, yttrium oxysulphide, yttrium aluminium gallium oxide (YAG), yttrium aluminium garnet, sodium yttrium fluoride (NaYF$_4$), lanthanum fluoride, lanthanum oxysulphide, yttrium fluoride (YF$_3$), yttrium gallate, gadolinium fluoride (GdF$_3$), barium yttrium fluoride (BaYF$_5$ or BaY$_2$F$_8$), gadolinium oxysulphide, zinc silicate, zinc sulphide and yttrium vanadate. The activator is generally a lanthanide or actinide moiety.

Other phosphors are organic chelates of lanthanide or actinide moieties. Light emission may be enhanced by combining or mixing the lanthanide or actinide chelate with a Lewis base enhancer such as for example an imido phosphorane. Examples of phosphors of this kind are described in EPA 556005. They may conveniently be used in solution or dispersion in polystyrene or other organic polymer.

The identity of the lanthanide or actinide moiety determines the emission wavelength of the phosphor. Preferred moieties are selected from terbium, europium, erbium, thulium, holmium, dysprosium, samarium, ytterbium, lutecium, gadolinium, uranium and uranyl $UO_2$, generally in the form of +2 or +3 ions.

EXAMPLE

Figure 1:
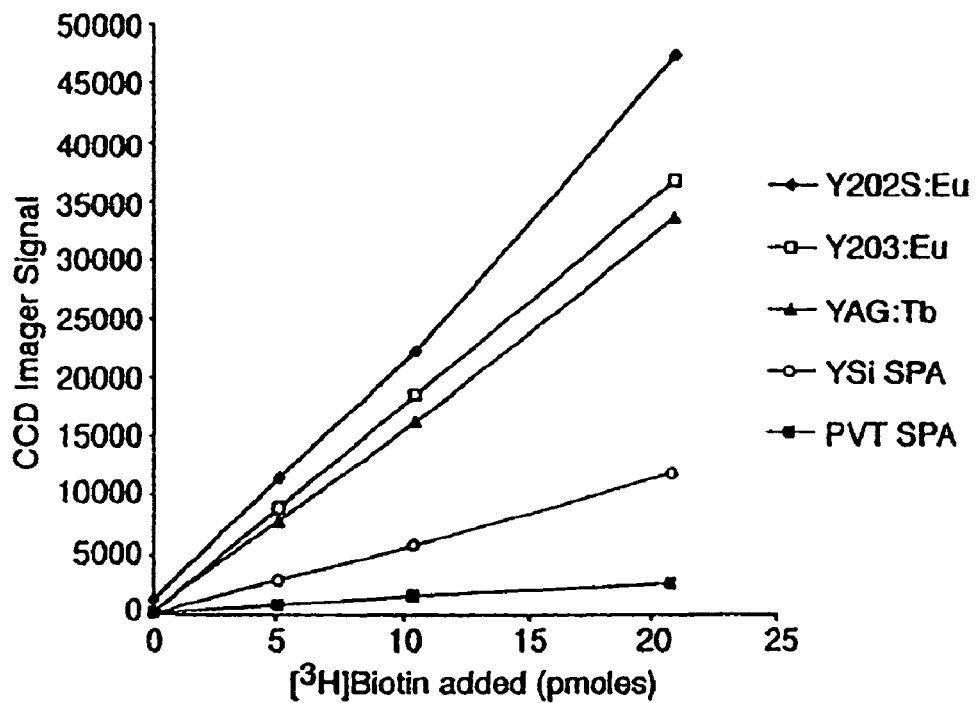
FIG. 1 shows CCD detected signal from inorganic phosphor particles with PVT SPA beads and yttrium silicate particles for comparison.

The present examples are provided for illustrative purposes only and illustrate certain embodiments of the instant invention. They are not intended to be illustrative of all embodiments of the present invention as recited in the claims.

Example 1

Comparison of CCD Detected Signal from [3H]biotin Bound to Streptavidin Coated Phosphor Particles, Streptavidin Coated Polystyrene Beads Containing Organic Chelates of Europium and Terbium and Streptavidin SPA Beads Introduction Inorganic phosphors Y2O3:Eu, Y2O2S:Eu and YAG:Tb and organic chelate beads prepared from polystyrene containing tris(2,2,6,6-tetramethyl-3,5-heptanedionato)terbium III-diphenyl-phosphonimido-triphenylphosphorane (hereafter called ALP-1) or tris(napthoyltrifluoroacetonato)europium III-(diphenyl-phosphonimido-triphenyl phosphorane)1 or 2 (hereafter called ALP-7 or ALP-7-diphos respectively) were surface-coated with streptavidin and were compared with streptavidin coated polyvinyl toluene (PVT) SPA beads and streptavidin coated yttrium silicate particles in a [3H]biotin binding assay. Coating of particles with proteins, such as streptavidin and other bioreactive species either covalently or by physical adsorption is accomplished by traditional methods known to those skilled in the art.

Materials and Methods

Inorganic phosphors used in example experiments are known materials and have been obtained from commercial suppliers in modified forms to facilitate their use in scintillation proximity assays. Organic chelate beads have been prepared by traditional methods known to those skilled in the art. The particles used for this experiment exemplify the CCD detection of the different reagents but are not necessarily optimal formulations of said reagents. The CCD imager used in the following examples is a prototype system supplied by Molecular Devices Inc. and incorporates a liquid nitrogen cooled CCD camera, supplied by Princeton Instruments Inc. Alternative CCD imager detection systems under development are expected to give similar relative response with the different types of particles and plates with enhanced sensitivity. For examples employing white walled microtitre plates an appropriate bandpass filter was used to eliminate phosphorescence from the plates.

Biotin Binding Assay

Streptavidin-coated particles and PVT SPA beads were suspended in phosphate buffered saline pH7.4 containing 0.01% w/v sodium azide (hereafter PBS azide) at 5 mg/ml. Stocks of [3H]biotin (Amersham TRK753) were made up in PBS azide to contain 5.1, 10.3 and 20.7 pmoles of biotin in 100 μl. Into the wells of a black microplate was pipetted 100 μl samples of particle suspensions. Particle suspensions were mechanically mixed to ensure homogeneity of samples. 100 μl of the each of the three [3H]biotin solutions was added to the wells containing the different particles. Following the additions the plate was sealed and then incubated on a microplate shaker for 60 minutes at room temperature. The SPA signal was detected using a CCD camera imaging system. Non specific binding of [3H] biotin to particles was examined by measuring signal detected in the presence of a large excess of unlabelled biotin. For all particles tested non specific binding of [3H] biotin was insignificant (not greater than 3% and typically not greater than 1% of signal from control wells).

Results

Figure 2:
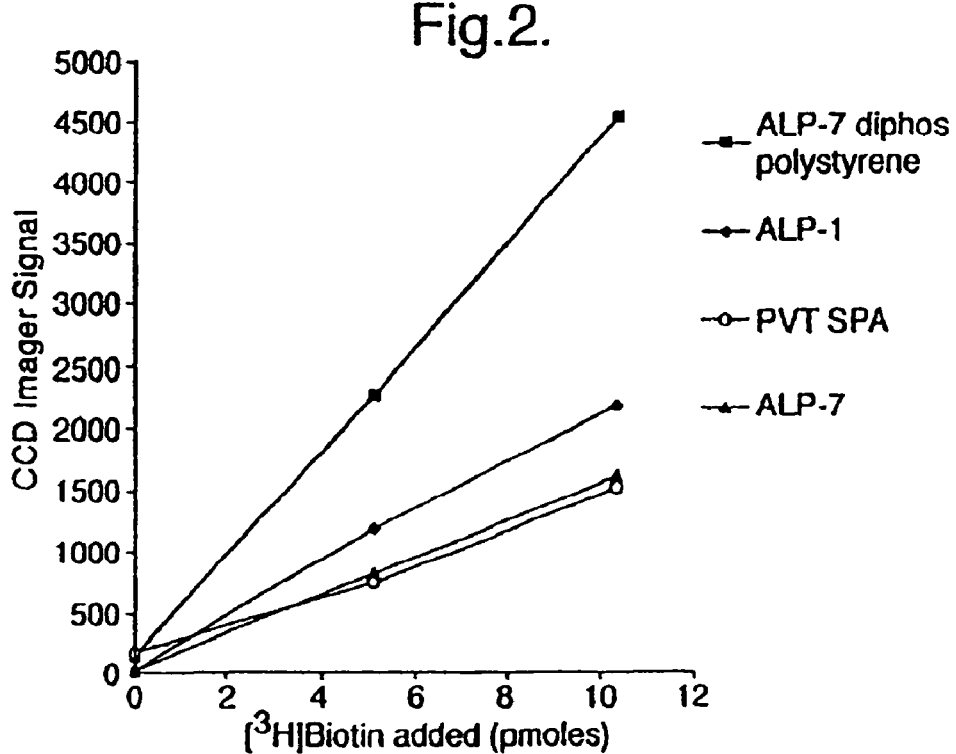
FIG. 2 shows CCD detected signal from organic chelate beads with PVT SPA beads for comparison.

The results, in FIGS. 1 and 2, show the imager signal generated using three levels of [3H]biotin bound to 500 μg of streptavidin coated phosphor particles, polystyrene particles containing organic chelates of europium and terbium and conventional SPA particles.

Conclusions

The data in Example 1 demonstrates that the CCD imager signal generated from [3H]biotin binding to streptavidin coated Y2O2S:Eu, Y2O3:Eu and YAG:Tb was at least 10 fold higher than the PVT SPA signal. Polystyrene/ALP-7-diphos beads generate approximately 3 times the signal of PVT SPA beads.

Example 2

Figure 3:
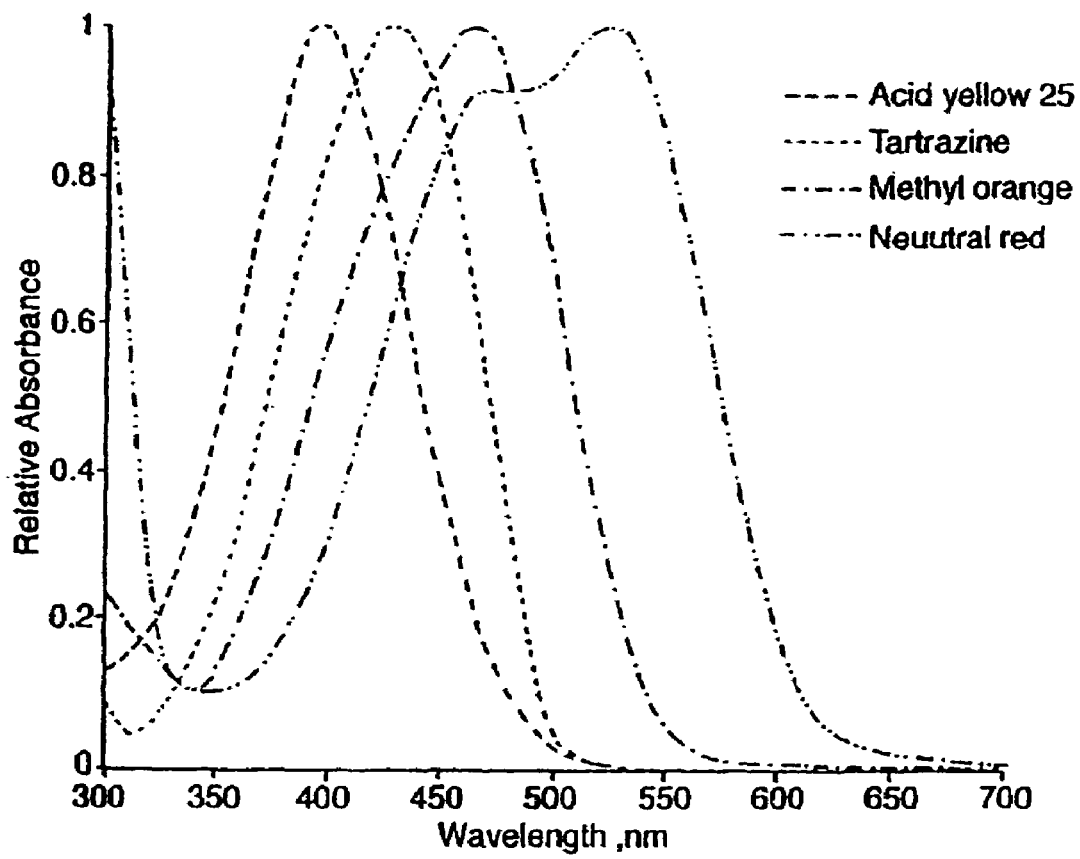
FIG. 3 shows absorbance spectra for dyes used in Example 2.
Figure 4:
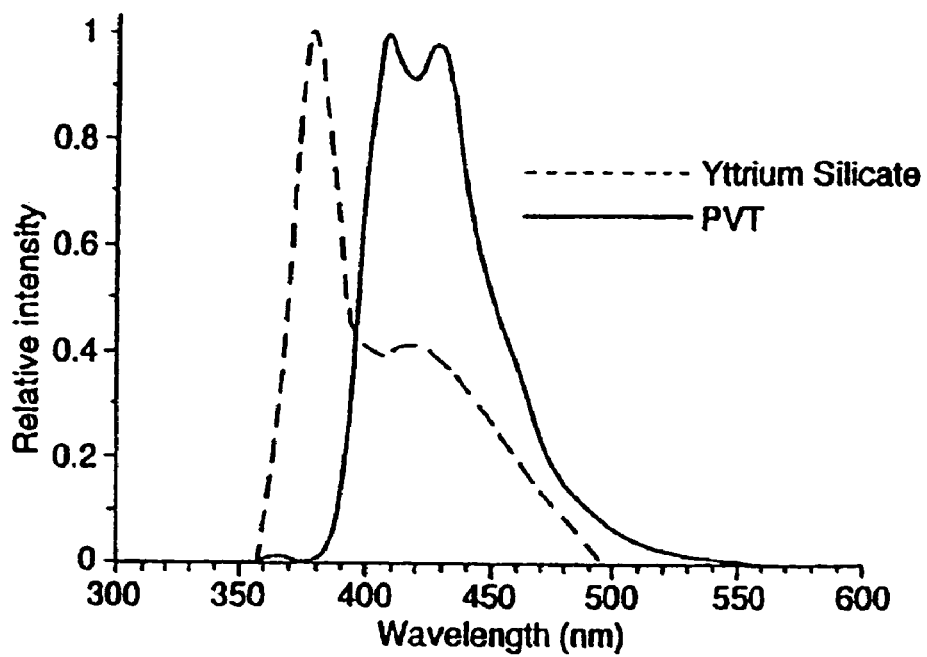
FIG. 4 shows emission spectra for PVT SPA, yttrium silicate particles, $Y_2O_3$:Eu and YAG:Tb particles.
Figure 4:
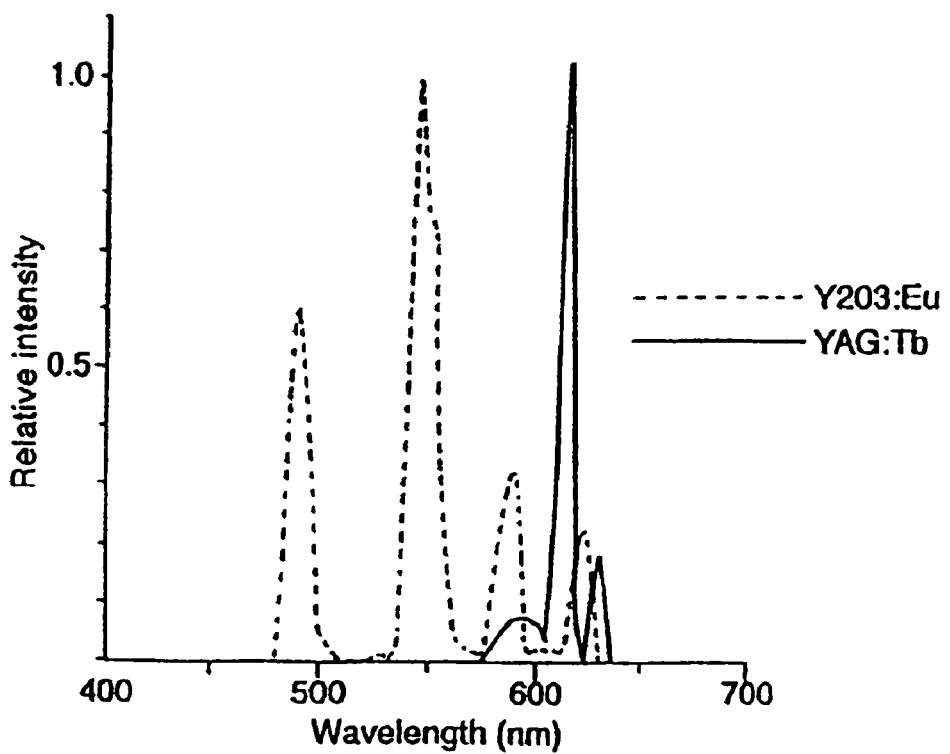

Colour Quench Effects of Yellow, Orange and Red Dyes in a Model [3H]biotin Binding Assay Introduction The quenching of signal (counts) by coloured compounds is a well known phenomenon in conventional scintillation counting. Spectral overlap of the emissions of scintillating materials with the absorption spectra of coloured materials is a prerequisite for this to be observed. Dyes have been chosen to cover the range of sample colours commonly encountered in SPA screening assays (see dye absorption spectra in FIG. 3 with the emission spectra of PVT SPA, yttrium silicate, $Y_2O_3$:Eu and YAG:Tb in FIG. 4 for reference). A model assay was set up to illustrate one of the advantages of the use of long wavelength emitting particles for signal detection, in the presence of coloured compounds with a CCD imager.

A [$^3$H]biotin binding assay was used to determine the effect of coloured compounds on the imager signal generated using phosphor particles $Y_2O_2$S:Eu, $Y_2O_3$:Eu and YAG:Tb compared to yttrium silicate and PVT SPA beads. Additionally the relative quenching of organic chelate polystyrene beads was compared to PVT SPA beads.

Materials and Methods

Streptavidin coated inorganic phosphor particles, organic chelate containing polystyrene, yttrium silicate and PVT SPA beads were suspended in PBS azide, at 5 mg/ml.

Acid yellow (Sigma A-4520) was dissolved in PBS azide at 360 µg/ml.

Tartrazine (Sigma T-0388) was dissolved in PBS azide at 214 µg/ml.

Methyl orange (Sigma M-3132) was dissolved in PBS azide at 196 µg/ml.

Neutral red (Raymond and Lamb lot 5769) was dissolved in PBS azide at 234 µg/ml.

[$^3$H]Biotin (Amersham TRK753) was diluted in PBS azide to 107 nM.

Assay Protocol

100 µl aliquots of each bead suspension (500 µg) was pipetted into the appropriate number of wells of black microplates followed by 100 µl of the stock of [$^3$H] biotin. Plates were incubated for approximately 30 minutes at ambient temperature, to allow complete binding of biotin to particles. 10 µl of the 4 dye solutions was added to the wells for each of the particles being tested with 10 µl of buffer added to control wells. Plates were incubated on a microplate shaker for 60 minutes at room temperature. The SPA signal was detected using the CCD imaging system.

In-well concentrations of dyes were set at levels that give an absorbance in the range 0.3 to 0.5 at the absorption maximum wavelength for each dye, when measured in a 1 cm path length spectrophotometer.

Results

The results, shown in Table 1, indicate that the europium containing phosphor particles or organic chelate beads do not show quenching of signal by the dyes tested in this experiment. PVT SPA beads and yttrium silicate particles, as employed in conventional SPA assays, exhibit marked quenching of signal by these dyes. Terbium containing phosphor particles and organic chelate beads are quenched to a small extent by neutral red dye. This latter observation would be expected from the partial overlap of the absorption spectrum of neutral red with the emission spectrum of terbium.

TABLE 1

Comparison of quenching of CCD detected signal from inorganic phosphors, organic chelate particles and PVT SPA beads and yttrium silicate by yellow, orange and red dyes.

| Bead Type | Acid Yellow 25 | Tartrazine | Methyl Orange | Neutral Red |
|---|---|---|---|---|
| $Y_2O_3$:Eu | No quench | No quench | 1% | No quench |
| YAG:Tb | No quench | No quench | No quench | No quench |
| $Y_2O_2$S:Eu | 3% | 4% | No quench | No quench |
| YSi SPA | 26% | 41% | 23% | 9% |
| PVT SPA | 19% | 10% | 11% | 25% |
| ALP-7 (Eu chelate) | No quench | No quench | No quench | No quench |
| ALP-1 (Tb chelate) | No quench | No quench | No quench | 10% |
| ALP-diphos polystyrene (Eu chelate) | No quench | No quench | No quench | No quench |

Conclusion

This example demonstrated that dyes which have an absorption spectrum overlapping with the emission spectrum of the scintillants in PVT SPA beads or yttrium silicate, can cause quenching of the emitted light from said species when excited by bound radiolabel. The CCD detected signal from europium or terbium containing phosphor particles or organic chelates of said materials incorporated in polymeric matrices was not significantly quenched in the presence of these dyes.

Example 3

Evaluation of Concentration Dependence of Signal Quenching by Tartrazine for Inorganic Phosphor Particles, ALP-7-diphos Beads and PVT SPA Beads and Yttrium Silicate Particles Introduction An experiment was set up to compare the concentration dependent quenching of signal from the different particles under investigation as detected by a CCD imager and a conventional scintillation counter.

Materials and methods

Streptavidin coated inorganic phosphor particles, ALP-7-diphos (polystyrene) beads, PVT SPA beads and yttrium silicate particles were suspended in PBS azide, at 10 mg/ml.

Tartrazine (Sigma T-0388) was dissolved in PBS azide at 1070 Tg/ml. [$^3$H]Biotin (Amersham TRK 753) was diluted in PBS azide to 103 nM.

Assay Protocol

100 µl aliquots of particle suspensions were pipetted into the appropriate number of wells of black microtitre plates. 100 µl of the stock solution of [$^3$H] biotin (10.3 pmoles) was added to each well. Plates were incubated at ambient temperature for 60 minutes to allow complete binding of biotin to particles. Tartrazine solution (1,2,4 or 8 µl) was pipetted into appropriate wells of the plate, with PBS azide added to a final volume of 208 µl per well. Triplicate data points were set up to contain 5.1, 10.2, 20.4 and 40.8 µg/ml of tartrazine respectively. The plates were incubated on a microplate shaker for 60 minutes at room temperature. The SPA signal was detected using a CCD imaging system. The plate was then counted on a Wallac MicroBeta™ scintillation counter.

Results

The results of this example are shown in Table 2. For yttrium silicate particles it is observed that high levels of signal quenching are observed in CCD detection (33–58%) and also under conventional SPA counting conditions (54–82%). The observed level of quenching of signal is related to the concentration of tartrazine present, with increasing levels of quench observed at increasing levels of added tartrazine. CCD detected signal for inorganic phosphor particles exhibit insignificant quenching of signal at the highest level of dye used (equivalent to approximately an absorbance reading of 2 at wavelength maximum in a 1 cm path length spectrophotometer). Quenching of CCD detected signal from PVT SPA beads (2–15%) is less pronounced than that observed for yttrium silicate particles but is still significant. Conventional scintillation counting of PVT SPA beads with the 4 levels of tartrazine present show very high signal quenching (37–87%) and exemplifies the requirement for colour quench correction for conventional SPA assays. ALP-7-diphos polystyrene beads do not show significant quenching of CCD detected signal in this experiment (not greater than 4%).

TABLE 2

Quenching emission of SPA particles by tartrazine at 4 different levels of dye. Comparison of quenching of signal detected by CCD detection and by a scintillation counter.

| | Tartrazine concentration, µg/ml | | | |
|---|---|---|---|---|
| | 5.1 | 10.2 | 20.4 | 40.8 |
| CCD Detection | | | | |
| $Y_2O_2S$:Eu | No quench | No quench | No quench | No quench |
| $Y_2O_3$:Eu | No quench | No quench | No quench | No quench |
| YAG:Tb | No quench | No quench | No quench | 3% |
| Ysi SPA | 33% | 44% | 52% | 58% |
| ALP-7-diphos polystyrene | No quench | 1% | 4% | No quench |
| PVT SPA | 2% | 4% | 6% | 15% |
| Microbeta, SPA mode | | | | |
| Ysi SPA | 54% | 61% | 73% | 82% |
| PVT SPA | 37% | 46% | 69% | 87% |

Conclusions

Colour quench correction is necessary to successfully carry out SPA assays using PVT SPA beads or yttrium silicate particles. For inorganic phosphors or organic chelate beads containing europium and terbium insignificant levels of quenching is observed. The requirement for colour quench correction with these materials, if CCD imager detection is employed, is therefore obviated.

Example 4

Assay of Reverse Transcriptase Utilising Streptavidin-coated Phosphor Particles

Introduction

The reverse transcriptase enzyme SPA assay (Amersham NK 8972) is a homogeneous assay system which uses a biotinylated DNA/RNA oligonucleotide enzyme substrate which is captured on streptavidin PVT SPA beads for quantification. Streptavidin-coated $Y_2O_3$:Eu and YAG:Tb particles were compared with streptavidin PVT SPA beads in this assay.

Materials and Methods

Reverse Transcriptase Assay

Biotinylated, ready annealed primer/template was added to the wells of a black microplate. This was followed by [$^3$H]TTP (Amersham TRK576) in 75 nM mixture of dATP, dCTP, dGTP and TTP buffered in 50 mM tris/HCl pH 8.0, 80 mM KCl, 10 mM $MgCl_2$, 10 mM DTT and 0.05% w/v Nonidet P40. The reactions were initiated with the addition of 0.075, 0.15 or 0.3 units of HIV reverse transcriptase (Amersham T3610Y). Plates were incubated at 37° C. for 30 minutes and were terminated with the addition of stop reagent. 0.5 mg of the appropriate streptavidin-coated phosphor or PVT SPA beads was added and the plates were incubated at room temperature for 10 minutes. The signal generated was detected using the CCD imaging system.

Results

Figure 5:
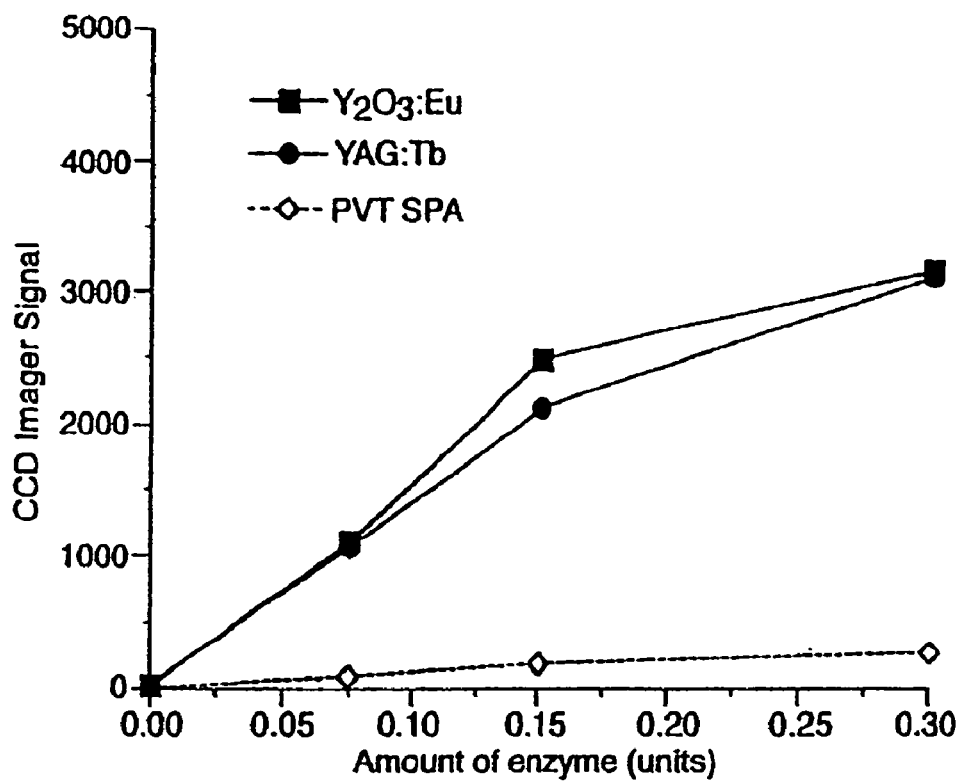
FIG. 5 shows evaluation of streptavidin coated inorganic phosphor particles in a reverse transcription scintillation proximity assay detected by a CCD imaging system.

The results, illustrated in FIG. 5, show the incorporation of radiolabelled nucleotide was dependent on the amount of reverse transcriptase enzyme used. The data shows maximum signals of 3,200, 3,100 and 300 were observed using 0.3 units HIV reverse transcriptase in a 30 minute assay with $Y_2O_3$:Eu and YAG:Tb and PVT SPA beads respectively.

Conclusion

This example shows the CCD imager signal generated in the reverse transcriptase SPA system was at least 10 fold higher using $Y_2O_3$:Eu and YAG:Tb than with PVT SPA beads.

Example 5

Assay of Reverse Transcriptase Inhibition by Aurintricarboxylic Acid, Utilising Streptavidin-coated Polystyrene Beads Introduction The reverse transcriptase enzyme SPA assay (Amersham NK8972) is a homogeneous assay system which uses a biotinylated DNA/RNA oligonucleotide enzyme substrate which is captured on streptavidin PVT SPA beads for quantification. In this assay, streptavidin-coated organic chelate beads prepared from polystyrene (PST) containing europium were used and the inhibition of reverse transcriptase by aurintricarboxylic acid determined.

Materials and Methods

Reverse Transcriptase Assay

Biotinylated, ready annealed primer/template was added to the wells of a white microplate. This was followed by [$^3$H]TTP (Amersham TRK576) in 127 nM mixture of dATP, dCTP, dGTP, and TTP buffered in tris/HCl pH 8.0, 80 mM KCl, 10 mM $MgCl_2$, 10 mM DTT and 0.05% w/v Nonidet P40. Aurintricarboxylic acid at concentrations between 0.05 and 1 µM was added and the reactions were initiated by the addition of 0.05 units of HIV reverse transcriptase (Amersham T3610Y). Plates were incubated at 37° C. for 20 minutes and were terminated with the addition of stop reagent. 0.1 mg of streptavidin coated PST beads was added and the plates were incubated overnight at room temperature. The signal generated was detected using the CCD imaging system.

Results

Figure 6:
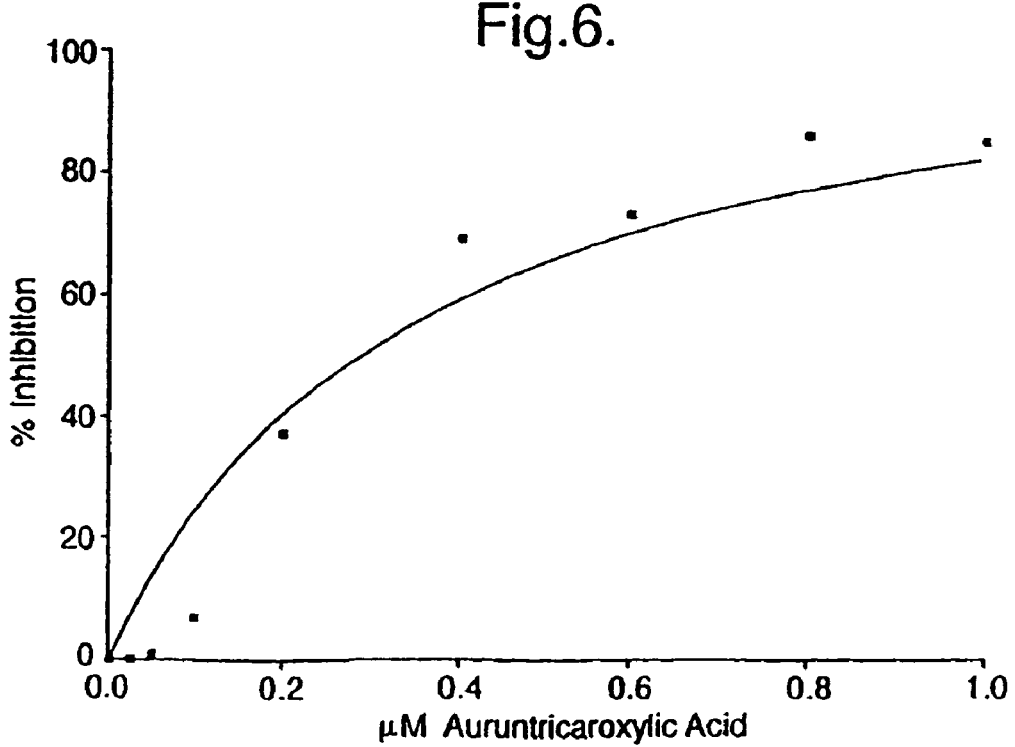
FIG. 6 shows inhibition of HIV reverse transcriptase by aurintricarboxylic acid, using streptavidin coated polystyrene beads and CCD imaging.

The results, illustrated in FIG. 6, show the inhibition of reverse transcriptase activity by aurintricarboxylic acid. The data shows that 85% inhibition can be achieved with 1 μM of inhibitor and $IC_{50}$ value of 0.23 μM was determined. This is comparable to the value of 0.18 μM determined for the SPA assay.

Conclusion

This example shows that polystyrene europium beads and a known inhibitor of reverse transcriptase can be used to determine $IC_{50}$ values in the reverse transcriptase SPA assay with CCD imaging.

Example 6

Evaluation of the GTPγS G-protein Coupled Receptor Assay Using Wheat Germ Agglutinin (WGA)-coated Polystyrene Beads Introduction The GTPγS G-protein coupled receptor SPA assay (Amersham RPNQ0210) is a homogeneous assay system which uses wheat germ agglutinin (WGA)-coated PVT SPA beads to bind receptor. Agonist-induced or inverse agonist-induced activity for receptors coupled to GTP-binding proteins (G-proteins) can be quantified directly in the presence of added $[^{35}S]$ GTPγS and GDP. Coated organic chelate beads prepared from polystyrene (PST) containing europium were therefore compared with WGA-coated PVT SPA beads in this assay.

Materials and Methods

GTPγS G-protein Coupled Receptor SPA Assay 3.75 μg of cloned rat adenosine A1 receptor (BioSignal BSR-MA1R), 0.375 mg of appropriate WGA-coated bead, 10 μM of (−)-$N^6$-(2-phenylisopropyl-adenosine) (PIA) agonist, 5 μM of GDP, +/−10 μM of GTPγS (to determine non-specific binding) and 0.2–0.4 nM of $[^{35}S]$GTPγS were added to the wells of a white microplate in a final volume of 50 μl of assay buffer, comprising of 20 mM HEPES, 100 mM NaCl, 10 mM $MgCl_2$ and 1 mM EDTA pH7.4. Plates were incubated at room temperature for 30 minutes and then centrifuged for 10 minutes at 1200 rpm and 15° C. The signal generated was detected using the CCD imaging system.

Results

Figure 7:
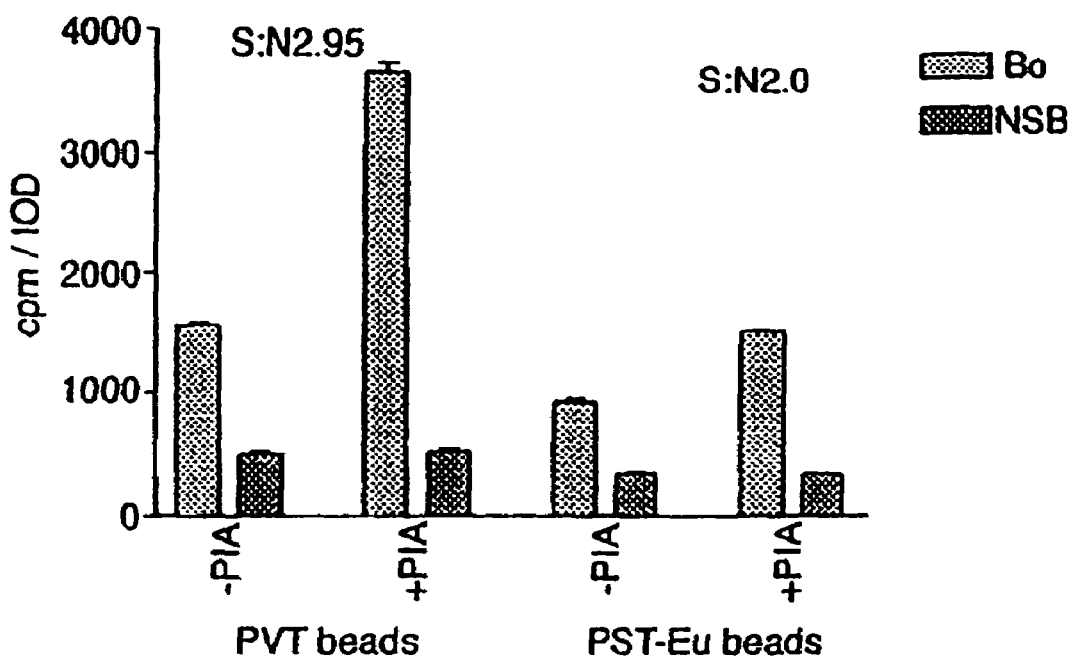
FIG. 7 shows comparison of CCD detected signal; from PST WGA coated beads and ChOAl receptor/PIA agonist in the [$^{35}$S]GTPγS G-protein coupled receptor assay with scintillation counting signal of PVT WGA coated SPA beads.

The results, illustrated in FIG. 7, show the scintillation counter and imager signals generated in the GTPγS G-protein coupled receptor SPA assay in the presence and absence of PIA agonist using WGA-coated PST imager beads and PVT SPA beads. The data shows that a similar signal to noise ratio can be achieved in the imaged assay to that achieved in the SPA assay.

Conclusion

This example shows that polystyrene europium beads can be used with $[^{35}S]$ radiolabel in a miniaturized receptor assay to give a comparable signal to noise ratio to that obtained with conventional SPA.

Example 7

Assay of Epidermal Growth Factor (EGF) Binding to EGF Receptor, Using Wheat Germ Agglutinin (WGA)-coated Organic Polystyrene Beads Containing Organic Chelates of Europium Introduction The interaction of $[^{125}I]$ EGF (Amersham IM196) with EGF receptor (EGF-R) expressed by the A431 human cell line can be studied using SPA in a homogeneous assay system in which the receptor is captured onto WGA-coated PVT SPA beads. In this assay, WGA-coated organic chelate beads prepared from polystyrene (PST) containing europium were used and the inhibition of $[^{125}I]$ EGF binding by unlabelled EGF determined.

Materials and Methods

EGF Receptor Assay

25 μg of A431 membrane (in house preparation) was pre-coupled to 0.25 mg of WGA-coated PST bead for 2 hours at room temperature. This was then transferred to a white microplate and 400 μM of $[^{125}I]$ EGF (Amersham IM196) added in assay buffer, comprising of 20 mM HEPES pH7.5, 2 mM $CaCl_2$, 0.1% (w/v) BSA fraction V, with unlabelled EGF at concentrations between 0 and 100 nM. Plates were incubated at room temperature for 3 hours and the signal generated detected using the CCD imaging system.

Results

Figure 8:
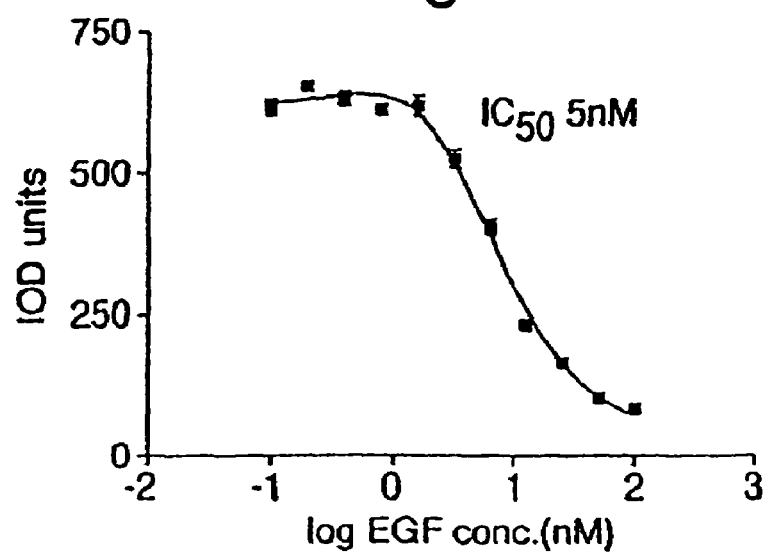
FIG. 8 shows inhibition of [$^{125}$I]EGF binding to WGA-coated polystyrene beads using CCD imaging.

The results, illustrated in FIG. 8, show the inhibition of $[^{125}I]$ EGF binding to WGA-coated PST beads. From the data, an $IC_{50}$ value of 5 nM was determined which is comparable to the value of 2 nM determined for the SPA assay.

Conclusion

This example shows that polystyrene europium beads and unlabelled EGF can be used to determine $IC_{50}$ values in the $[^{125}I]$ EGF receptor binding assay with CCD imaging.

Example 8

Assay of Mitogen Activated Protein (MAP) Kinase Enzyme Assay Utilising Streptavidin-coated Organic Polystyrene Beads and Streptavidin-coated Inorganic Phosphor Particles Introduction The mitogen activated protein (MAP) kinase SPA $[^{33}P]$ assay (Amersham RPNQ0220) is a homogeneous assay system which uses streptavidin-coated PVT SPA beads to bind $[^{33}P]$-labelled biotinylated myelin basic protein (bMBP) substrate. In this assay, streptavidin-coated organic chelate beads prepared from polystyrene (PST) containing europium and inorganic phosphor particles doped with europium were compared with streptavidin-coated PVT SPA beads in this assay.

Materials and Methods

MAP Kinase Assay

Reaction buffer containing 50 pmols of bMBP substrate, 25 pmols of ATP, 250 nmols $MgCl_2$ and 50 mM MOPS was added to the wells of a white microplate. 0.1 μCi of $[^{33}P]$ ATP (BF1000) and ERK-1 enzyme, at 0.01 μg to 2 μg, were then added. Plates were incubated at 37° C. for 30 minutes and the reaction terminated by addition of stop buffer containing 50 mM ATP and 0.25 mg of each bead type. The plates were then centrifuged for 10 minutes at 800 rpm and 15° C. The signal generated was detected using the CCD imaging system.

Results

Figure 9:
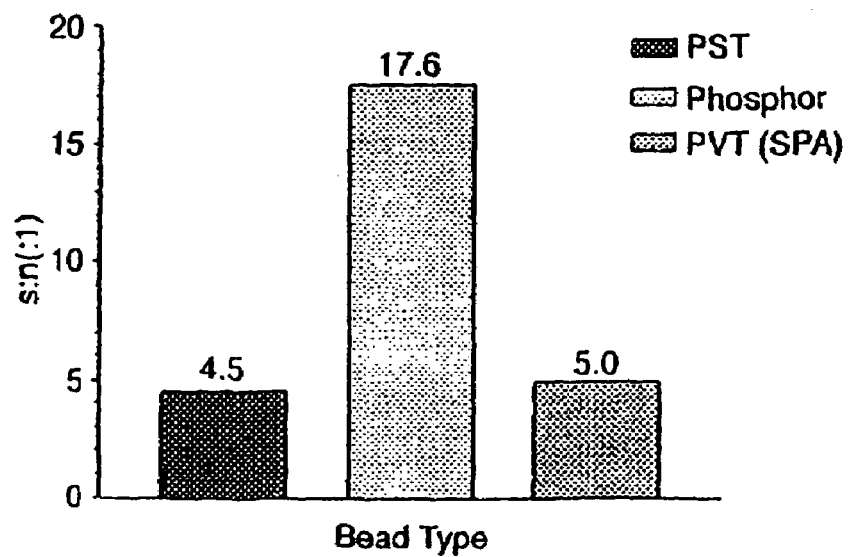
FIG. 9 shows comparison of signal to noise ratios obtained from PST streptavidin-coated beads and streptavidin-coated phosphor particles with CCD imaging and PVT streptavidin-coated SPA beads and scintillation counting.

The results, illustrated in FIG. 9, show the signal to noise ratios generated in the MAP kinase enzyme assay using streptavidin-coated PST and phosphor imager beads and PVT SPA beads. The data shows that a similar or better signal to noise ratio can be achieved in the imaged assay to that achieved in the SPA assay.

Conclusion

This example shows that both phosphor particles and polystyrene europium beads can be used with [$^{33}$P] radiolabel in a miniaturized enzyme assay to give a comparable or better signal to noise ratio to that obtained with conventional SPA.

Example 9

Comparison of 2% $^w$/w ALP-1 and Cytostar-T Microplates to Monitor the Uptake of [$^{14}$C]thymidine in Proliferating Cells Using a CCD Imaging System Introduction White 96-well microplates which were manufactured to incorporate the scintillant ALP-1 in the plate base were evaluated in Cytostar-T applications. 2% $^w$/w-ALP-1 plates were compared with Cytostar-T plates in a [$^{14}$C]thymidine uptake assay using adherent cells.

Materials and Methods

Routine Cell Growth Conditions

V-79 cells (ECACC no.86041102) were routinely grown at 37° C. in a humidified 5% $CO_2$ incubator in DMEM (ICN/FLOW 12-332-54) supplemented with 10% FBS (GIBCO/BRL 10099-117), 2 mM L-glutamine (ICN/FLOW 16-801-49), 50 IU/ml penicillin and 200 µg/ml streptomycin (ICN/FLOW 16-700-49). For routine subculture cells were passaged at 1:20 to 1:40 dilution.

Thymidine Uptake Assay

V-79 cells were seeded at 1×10$^4$/well into 2% $^w$/w ALP-1 and Cytostar-T plates and were incubated for 24 hours at 37° C. with 5% $CO_2$. Following this initial incubation 0.5 µCi [$^{14}$C]thymidine (Amersham CFA532) was added to the cells. Thymidine uptake was followed over 24 hours by counting the plates at intervals. The plates were incubated at 37° C. with 5% $CO_2$ when not being counted. The signal generated was counted using the CCD imaging system.

Results

Figure 10:
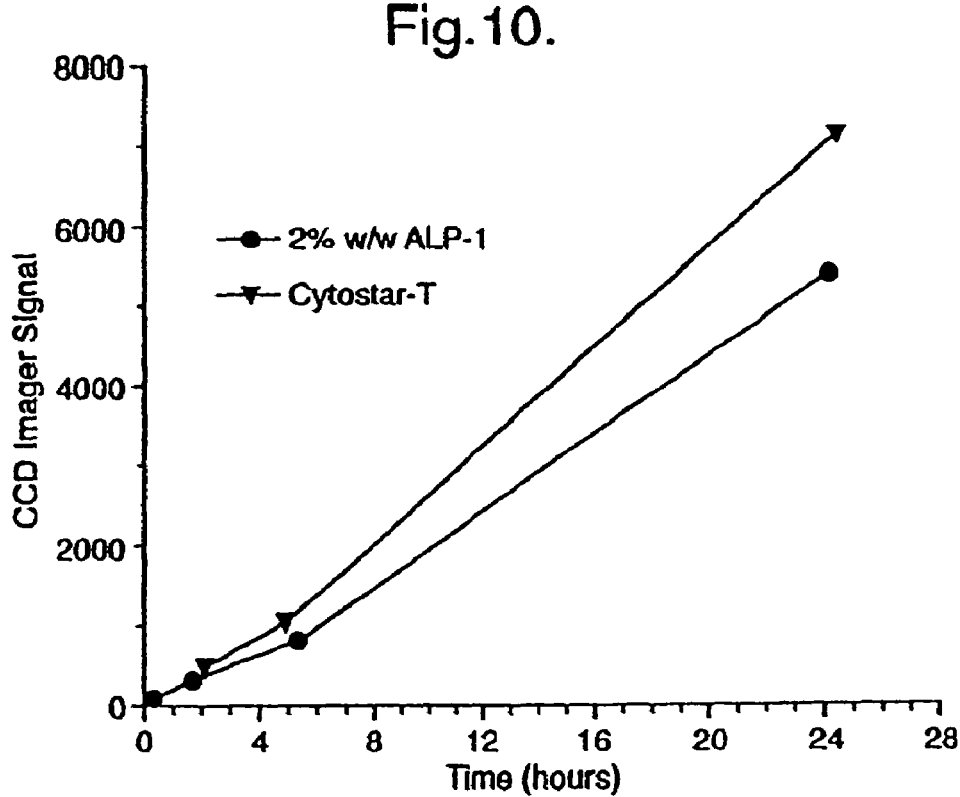
FIG. 10 shows comparison of the use of 2% $^w$/w ALP-1 microplates and Cytostar-T plates used to monitor the uptake of [$^{14}$C] thymidine in proliferating cells, using a CCD imaging system.

The results in FIG. 10 show that [$^{14}$C]thymidine uptake by V-79 cells was dependent on the period of incubation. Maximum [$^{14}$C]thymidine uptake signals of 5437 and 6953 were observed for 2% $^w$/w ALP-1 and Cytostar-T plates respectively after 24 hours.

Conclusion

The data in this example shows that the CCD imager signal generated in a [$^{14}$C]thymidine uptake assay using a 2% $^w$/w ALP-1 plate was comparable to the Cytostar-T plate signal.

Example 10

Comparison of 2% $^w$/w ALP-1 and Cytostar-T Microplates to Monitor the Uptake of [$^{14}$C]methionine in Proliferating Cells Using a CCD Imaging System Introduction 2% $^w$/w ALP-1 plates were compared with Cytostar-T plates in a [$^{14}$C]methionine uptake assay. The procedures and conditions of Example 9 were used in this experiment.

Materials and Methods

Methionine Uptake Assay

V-79 cells were seeded at 5×10$^3$/well into 2% $^w$/w ALP-1 and Cytostar-T plates and were incubated for 24 hours at 37° C. with 5% $CO_2$. Following this initial incubation the medium was aspirated from the wells and the cell monolayer washed once with sterile phosphate buffered saline. 200 µl of methionine depleted DMEM (ICN/FLOW 16-422-49) containing 0.5µCi [$^{14}$C]methionine was added to the cells. The uptake was followed over 24 hours by counting the plates at intervals. The plates were incubated at 37° C. with 5% $CO_2$ when not being counted. The signal generated was counted using the CCD imaging system.

Results

Figure 11:
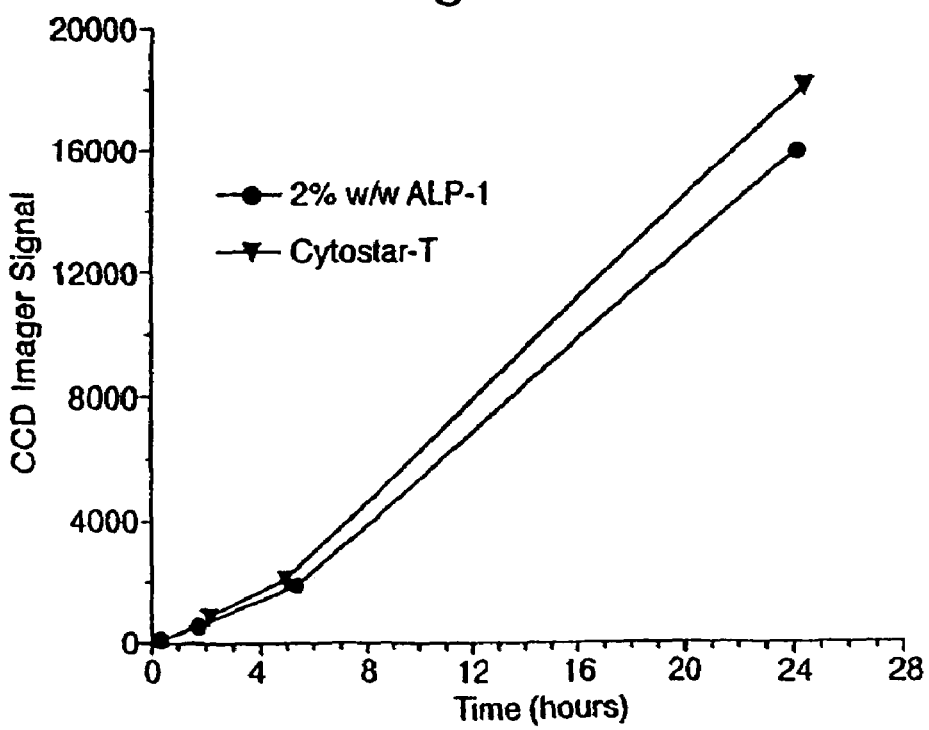
FIG. 11 shows comparison of the use of 2% $^w$/w ALP-1 microplates and Cytostar-T plates used to monitor the uptake of [$^{14}$C] methionine in proliferating cells, using a CCD imaging system.

The results in FIG. 11 show [$^{14}$C]methionine uptake was dependent on the period of incubation, with maximum uptake signals of 15865 and 18455 observed for 2% $^w$/w ALP-1 and Cytostar-T plates respectively after 24 hours.

Conclusion

In this example the results show that the CCD imager signal observed in a [$^{14}$C]methionine uptake assay using a 2% $^w$/w ALP-1 plate was comparable with the Cytostar-T plate signal.

Those skilled in the art, having the benefit of the teachings of the present invention as set forth above, can effect numerous modifications thereto. These modifications are to be construed as being encompassed within the scope of the present invention as set forth in the appended claims.

What is claimed is:

1. In a scintillation proximity method which uses a phosphor for detection, which method comprises the steps of:
   contacting a surface carrying said phosphor with a body of fluid containing a radioisotope to provide a reaction mixture;
   incubating said reaction mixture under conditions to allow binding of the radioisotope to the surface; and
   detecting radiation emitted by the phosphor;
   the improvement comprising using a phosphor that has an emission maximum of 480 nm–900 nm and a cooled charge coupled device for detecting radiation emitted by the phosphor as part of the detection system.

2. The method of claim 1, wherein the scintillation proximity test is performed in wells of a multiwell plate.

3. The method of claim 2, wherein the charge coupled device is used to simultaneously image all the wells of the multiwell plate.

4. The method of claim 1, wherein the phosphor has an emission maximum of 500 nm–700 nm.

5. The method of claim 1, wherein the phosphor is an inorganic host material doped with an activator which is a lanthanide or actinide moiety.

6. The method of claim 1, wherein the phosphor is an organic chelate of a lanthanide or actinide moiety.

7. The method of claim 5, wherein the lanthanide or actinide moiety is selected from the group consisting of terbium, europium, erbium, thulium, holmium, dysprosium, samarium, ytterbium, lutecium, gadolinium, uranium and uranyl $UO_2^{3+}$.

8. A method of performing a scintillation proximity test comprising:
   providing a solid surface comprising a phosphor in a fluid medium,
   causing a radiolabelled reagent to become divided into two fractions one bound to the solid surface and the other in the fluid medium, and
   detecting the fraction of the radio labelled reagent bound to the solid surface, characterised by using a phosphor that has an emission maximum of 480nm–900 nm and a cooled charge coupled device for detecting radiation emitted by the phosphor.

9. The method of claim 8, wherein the scintillation proximity test is performed in wells of a multiwell plate and the charge coupled device is used to image simultaneously all the wells of the multiwell plate.

10. The method of claim 8, wherein the phosphor is an organic chelate of europium or an inorganic host material doped with europium.

* * * * *